US005676149A

United States Patent [19]

Yao

[11] Patent Number: 5,676,149

[45] Date of Patent: Oct. 14, 1997

[54] METHOD OF COMPENSATING FOR INOPERATIVE ELEMENTS IN AN ULTRASOUND TRANSDUCER

[75] Inventor: Lin-Xin Yao, Bellevue, Wash.

[73] Assignee: Siemens Medical Systems Inc., Iselin, N.J.

[21] Appl. No.: 710,924

[22] Filed: Sep. 24, 1996

[51] Int. Cl.[6] .................... A61B 8/00

[52] U.S. Cl. .................... 128/660.01

[58] Field of Search .................... 128/660.01, 660.07, 128/661.01, 660.08; 73/631

[56] References Cited

U.S. PATENT DOCUMENTS 5,517,994 5/1996 Burke et al. .................... 128/660.01

*Primary Examiner*—George Manuel

[57] ABSTRACT

A method for compensating for inoperative transducer elements in an ultrasound transducer. The transmit voltage of the driving signals applied to transducer elements that are adjacent an inoperative element is increased to compensate for the inoperative element. Preferably, a linear interpolation used whereby the power/gain of the signals to be applied to the inoperative element is divided equally among the adjacent operative elements. If an inoperative transducer element is adjacent more than one inoperative element, then the gain of the operative transducer element is increased accordingly for each such inoperative element. In addition, the gain of the echo signals produced by the adjacent transducer elements is increased to compete for the inoperative element.

5 Claims, 5 Drawing Sheets

METHOD OF COMPENSATING FOR INOPERATIVE ELEMENTS IN AN ULTRASOUND TRANSDUCER

FIELD OF THE INVENTION

The present invention relates to ultrasound systems in general, and in particular to methods of compensating for inoperative elements in a ultrasound transducer.

BACKGROUND OF THE INVENTION

Ultrasound is an increasingly used tool for noninvasively examining a patient's body. A typical ultrasound system works by transmitting high frequency acoustic signals into the body and detecting and analyzing the returned echoes. To create an image of the tissue in the body, the strength of the ultrasonic echo from a given point is determined and used to modify the brightness of one or more pixels in a digital display screen.

To create an image of a patient's internal body matter, a beam of ultrasonic energy is delivered into a patient from an ultrasound transducer. A typical ultrasound transducer comprises an array of 128 to 256 transducer elements which are commonly made of piezoelectric crystals. Each crystal is supplied with an electronic driving signal that causes the crystal to vibrate and produce an ultrasonic sound wave. By controlling the time at which the driving signals are applied to the crystals, a beam of ultrasonic sound waves can be focused at any desired location in the body. Target elements, such as, tissue, bone, moving blood, etc., reflect a portion of the beam back to the transducer. The reflected beam causes the piezoelectric crystals to vibrate and in turn create received echo signals. The echo signals are focused and analyzed to create an ultrasound image that is displayed for a doctor or ultrasound technician.

Given the number of piezoelectric crystals found in an ultrasound transducer, it is inevitable that one or more of the transducer elements will inevitably malfunction and become inoperative. As will be described below, the images created with a transducer having inoperative crystals have a decreased resolution compared to images obtained with a fully operational transducer. Because it is prohibitively expensive to replace a transducer when one or two of the crystals fail, there is a need for a method of compensating for the inoperative crystals so that a transducer having one or more inoperative elements can be used to produce high quality ultrasound images.

SUMMARY OF THE INVENTION

The present invention is a method of compensating an ultrasound transducer having one or more inoperative transducer elements. To compensate for the inoperative elements, the voltage of the driving signals and the gain of the received echo signals is increased for those elements that are adjacent to an inoperative transducer element. The level of increase is determined by dividing the level of the transmit voltage and the receive gain that would have been applied to the inoperative element between the adjacent elements. By increasing the transmit voltage and receive gain, the beam pattern produced by the transducer is improved, and the quality of the ultrasound image is enhanced.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENT

As indicated above, the present invention is a method adjusting the driving signals that are applied to an ultrasound transducer as well as the gain of the signals produced by the transducer in order to compensate for one or more inoperative transducer elements. By increasing the transmit voltage and the receive gain of the transducer elements that are adjacent the inoperative elements, the quality of the transmit and receive beams produced by the transducer is improved.

Figure 1:
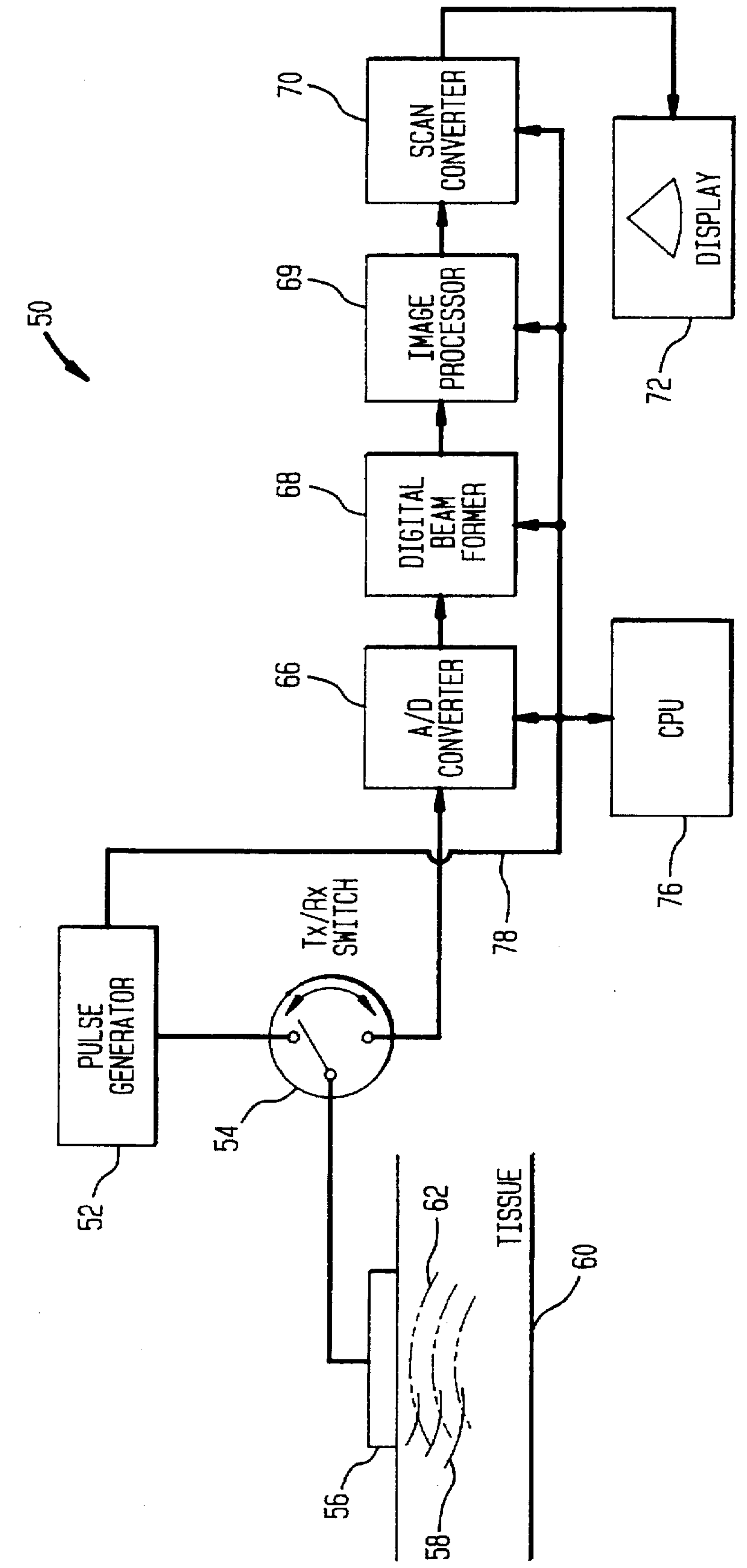
FIG. 1 is a simplified block diagram of an ultrasound system in which the present invention is used.

FIG. 1 is a simplified block diagram of an ultrasound system according to the present invention. The ultrasound system 50 includes a pulse generator 52 that generates a series of electronic driving signals that are optimized to produce echoes that can be detected and converted into an ultrasound image. The output of the pulse generator 52 is fed to a transmit/receive switch 54 that has two positions. In the first position, the output of the pulse generator is coupled to an ultrasound transducer 56 which comprises an array of transducer elements. Each transducer element is a piezoelectric crystal that converts the electronic driving signals received from the pulse generator into an ultrasonic sound wave 58 that is directed into the patient's body tissue 60. An ultrasonic echo 62 is created by reflections off the internal body matter of the patient and is received by the transducer elements. The received echo causes transducer elements to vibrate which in turn creates a number of electronic echo signals that are analyzed by the ultrasound system to produce the ultrasound image.

When the transmit/receive switch 54 is in the second position, the electronic echo signals produced by the transducer in response to a received echo are coupled to a receiver channel that includes an analog-to-digital converter 66. The analog-to-digital converter samples the signals produced by the transducer to produce a sequence of binary numbers representative of the received echoes. The output of the analog-to-digital converter 66 is fed to a digital beam former 68 that adjusts the gain of the digitized samples and selects samples of the digitized signals received from each of the transducer elements and combines them to form to a single binary number that is representative of the echo intensity at a particular position in the body tissue. The output of the digital beam former is fed to a signal processor 69 which detects and converts the data received from the beam former into pixel intensity values corresponding to the body tissue's characteristics. The scan converter 70 converts the data into the right format and transmits the data to a display screen 72 in order to produce the ultrasound image.

Controlling the operation of the ultrasound system 50 is a central processing unit 76 having its own internal and external memory in which data and the operating instructions of the CPU are stored. The CPU 76 is coupled to the pulse generator 52, analog-to-digital converter 66, beam former 68 and scan converter 70 by a common data/address bus 78. In addition, the CPU may be coupled to a mass storage device such as a hard drive, a communication circuit for transmitting and receiving data from a remote location and a video tape recorder for recording the ultrasound images produced.

Figure 2:
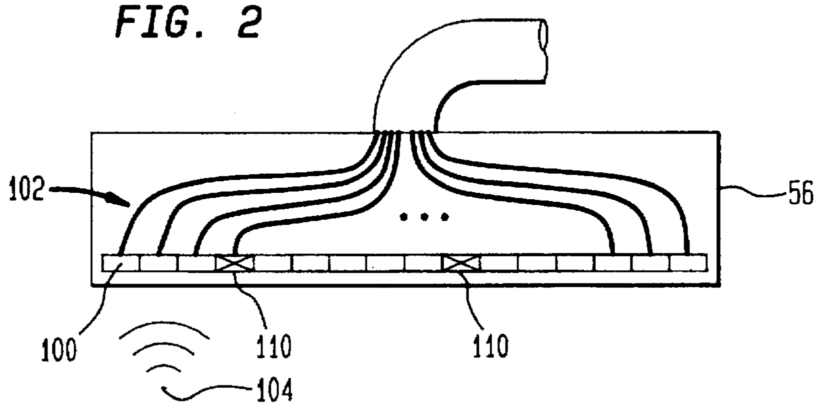
FIG. 2 illustrates an array of transducer elements found in a conventional ultrasound transducer.

FIG. 2 shows in greater detail an ultrasound transducer used to transmit and receive ultrasonic signals from the patient's body tissue. The transducer 56 comprises a number of transducer elements 100 that convert the driving signals received from the pulse generator into ultrasonic sound waves as well as convert the received echoes into electronic signals that are used to create an ultrasound image. Each of the transducer elements 100 is coupled to the pulse generator or analog-to-digital converter by a separate lead 102. The pulse generator 52 shown in FIG. 1 controls the timing and magnitude of the driving signals applied to each of the transducer elements so that an ultrasonic transmit beam is focused at a desired location in the patient's body. The focal point of the receive beam is continually changed along a beam line 104 to produce a series of data used to produce a single vertical column of pixels in the corresponding ultrasound image. To produce an entire ultrasound image, many beam lines are required.

Not all the transducer elements are used to create a beam line. Typically, only a portion of the elements that are centered about the beam line are used to generate the ultrasonic signal on the beam line and receive the reflected echoes from the target elements that lie on or near the beam line.

As indicated above, there may be as many as 128 or 256 transducer elements in a typical ultrasound transducer. Over time, it is inevitable that one or more elements 110 will malfunction and become inoperative. In the past, if a transducer element was inoperative, the ultrasound system simply attempted to form the transmit beam and the ultrasound image without any type of compensation.

Figure 3A:
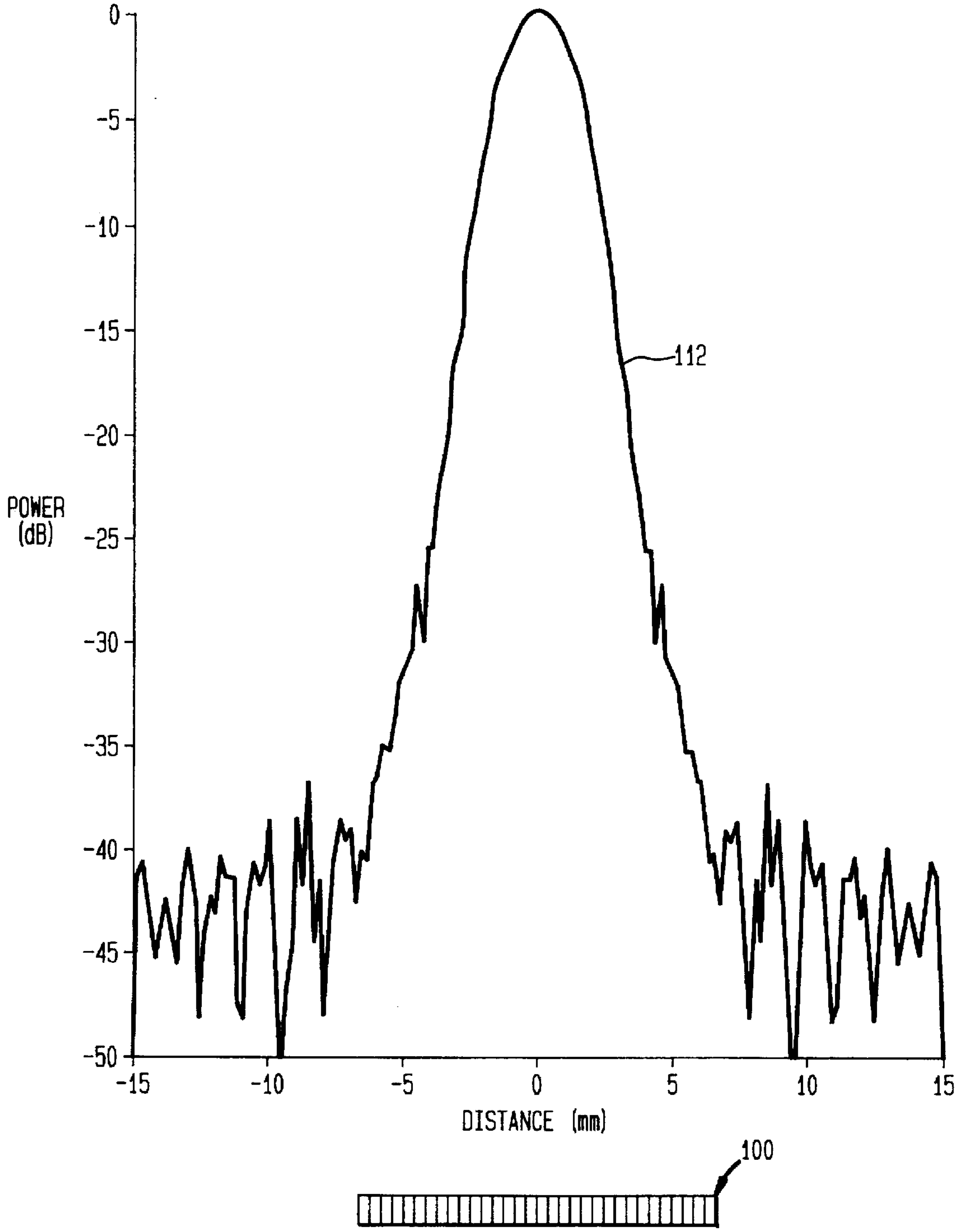
FIG. 3A is a graph illustrating an ultrasonic beam pattern created by an ultrasound transducer with 32 operating transducer elements.

FIG. 3A is a graph that illustrates a simulated one way ultrasonic beam pattern 112 formed by a transducer apeture having thirty-two operative transducer elements with a Haming apodization window. In the presently preferred embodiment of the invention, each transducer element is a piezoelectric crystal with a width of approximately 0.44 millimeters. The thirty-two transducer elements 100 are shown below the beam pattern to provide a sense of the relative size of the beam compared to the size of the elements themselves. The ultrasonic beam is created by applying the driving signals to each of the thirty-two working transducer elements in a proper timing to focus the beam at 6 centimeters.

With all thirty-two transducer elements working, the ultrasonic beam 112 produced has a beam width of approximately 10 millimeters at a −20 dB level. Outside of an area more than 5 millimeters from the center of the beam, the strength of the beam is more than −30 dB below its peak power.

Figure 3B:
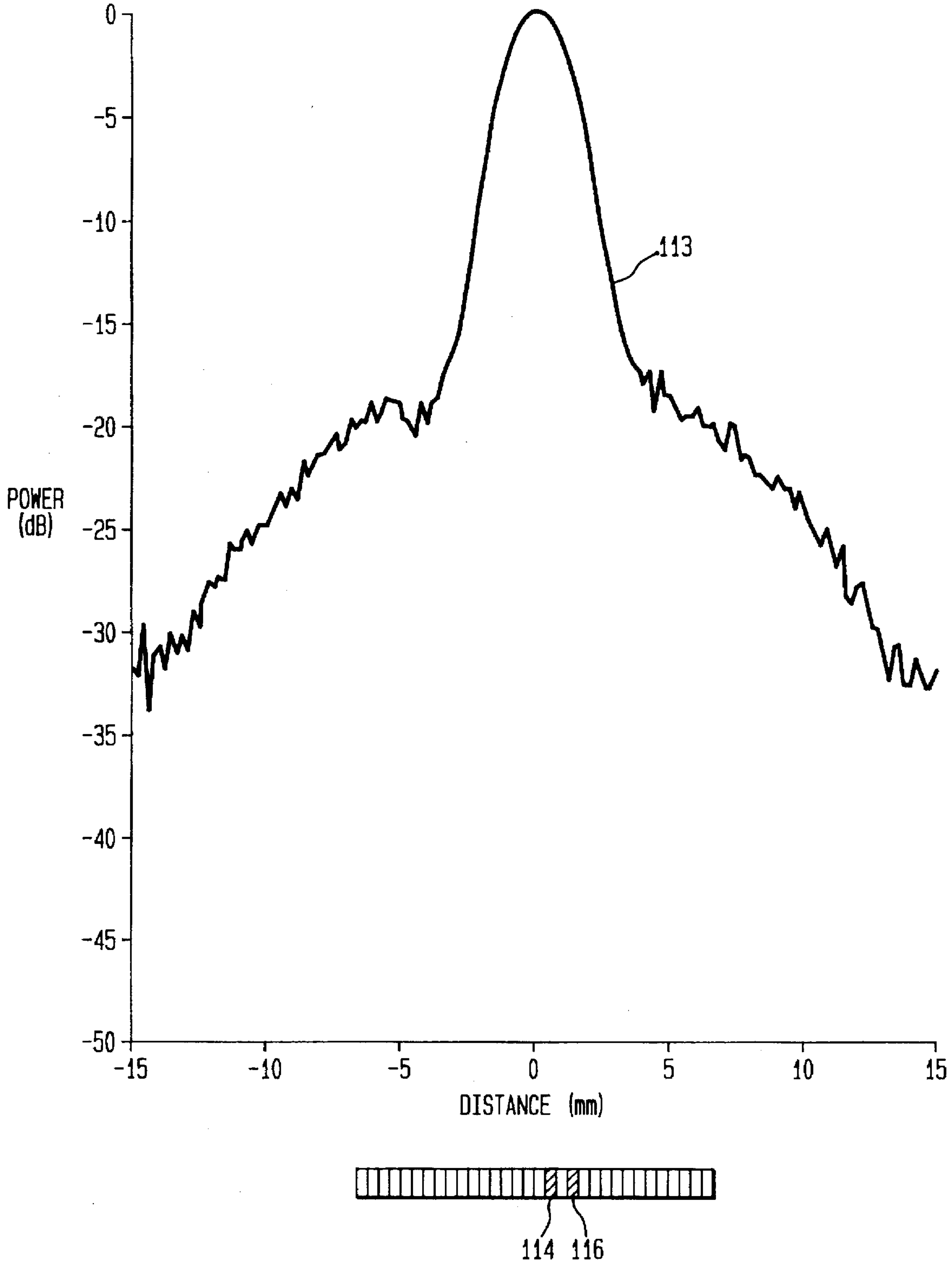
FIG. 3B is a graph illustrating a deteriorated beam pattern obtained using an ultrasound transducer with inoperative transducer elements.

FIG. 3B illustrates the deterioration of a simulated ultrasonic beam 113 that occurs when one or more of the transducer elements is inoperative. The graph in FIG. 3B was created on a computer system assuming a transducer having thirty-two transducer elements, all of which are driven with the same driving signals used to simulate the beam 112 shown in FIG. 3A. However, the beam pattern 113 was created assuming that two elements 114 and 116 of the original thirty-two are inoperative. As can be seen, the resulting beam pattern 113 created by the transducer having the inoperative elements is not as focused. The power of the beam 113 at a distance more than 5 millimeters from the center of the beam is only −20 dB below the peak power.

An ultrasound image created with the ultrasonic beam 113 shown in FIG. 3B will be somewhat smeared compared to an image created with the beam 112 shown in FIG. 3A. This smearing of the ultrasound image reduces the ability of the ultrasound system to resolve small objects, thereby impairing the ability of the physician or sonographer to clearly view details of the internal body matter of the patient.

Figure 4A:
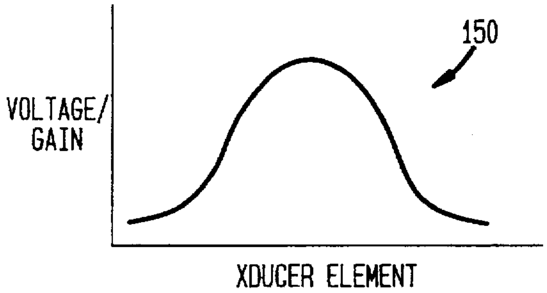
FIG. 4A is a graph of a typical driving signal applied to the ultrasound transducer to create an ultrasonic beam.

FIG. 4A shows a profile 150 of a driving signal that is actually used to excite the individual transducer elements in order to produce a quality ultrasonic echo. The profile also represents the relative gain applied to each of the signals produced by the transducer elements. The profile of the transmit voltage/receive gain is generally bell-shaped with the elements positioned over the center of the beam receiving more transmit voltage and receive gain than those transducer elements at the edges of the beam.

Figure 4B:
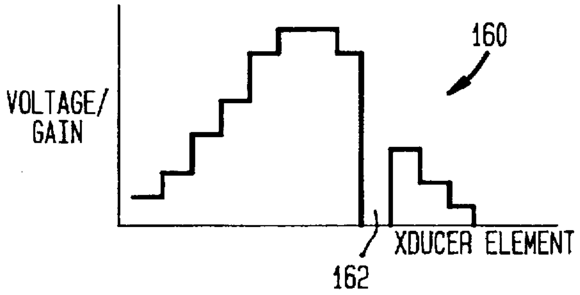
FIG. 4B shows the result when the driving signal shown in FIG. 4A is applied to an ultrasound transducer containing a inoperative element.

FIG. 4B shows a profile 160 that represents the effect of applying the driving signal shown in FIG. 4A to a transducer having an inoperative transducer element. The profile 160 is a discrete version of the driving signal shown in FIG. 4A. As can be seen, the profile 160 is roughly bell-shaped and is symmetric about the center of the beam line with the peak power being delivered to the transducer elements positioned directly over the center of the beam line. However, the profile 160 contains a gap 162 that occurs where the driving signal is applied to an inoperative transducer element. As indicated above, the result of applying a driving signal to a transducer with an inoperative element is that the image is smeared compared to the image that would be produced if all the transducer elements in the ultrasound transducer were working.

Figure 4C:
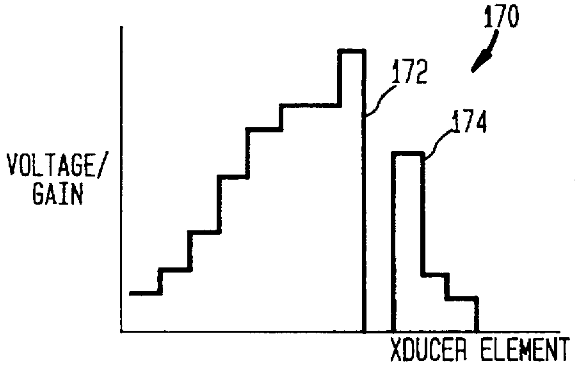
FIG. 4C shows a driving signal produced according to the present invention in order to compensate for the inoperative element in a transducer.

To compensate for an inoperative transducer element, the ultrasound system of the present invention uses a compensated driving signal and receive gain having a profile 170 as shown in FIG. 4C. The profile 170 is similar to the profile 160 shown in FIG. 3B with the exception that additional transmit voltage is applied to the transducer elements adjacent the inoperative element and the gain of the echo signals produced by the adjacent elements is also increased. The profile 170 contains two peaks, 172 and 174, that represent an increased transmit voltage and receive gain applied to the transducer elements located adjacent the inoperative transducer element. By increasing the transmit voltage and receive gain for those transducer elements that are adjacent the inoperative element, the resulting transmit and receive beam is made more focused and therefore the resulting image will have a higher resolution.

In the presently preferred embodiment of the invention, the increased transmit voltage/receive gain for the transducer elements that are adjacent an inoperative element is determined by using a linear interpolation. For example, if the transmit voltage of the driving signal that is supposed to be applied to an inoperative transducer element has a value of ten volts, then the transmit voltage of each of the adjacent transducer element is increased by five volts. In the event that a transducer element is adjacent to more than one inoperative element, then the transmit voltage of the working element is increased for each inoperative transducer element. The same is true for the receive gain, whereby the gain of the signals produced by the adjacent elements is determined by dividing the gain for the inoperative element equally among the adjacent elements.

To implement the method of the present invention, the ultrasound system must first detect which transducer elements are inoperative. To do this, the central processor analyzes the digitized signals produced by each transducer element. If an element does not produce any signal or a signal that has a constant value, it is assumed that the transducer element is not working. To compensate for the inoperative elements, the central processor programs the pulse generator 52 (shown in FIG. 1) to increase the transmit voltage and the beam former 68 to increase the receive gain of the working elements adjacent to the inoperative element as described above.

Figure 5:
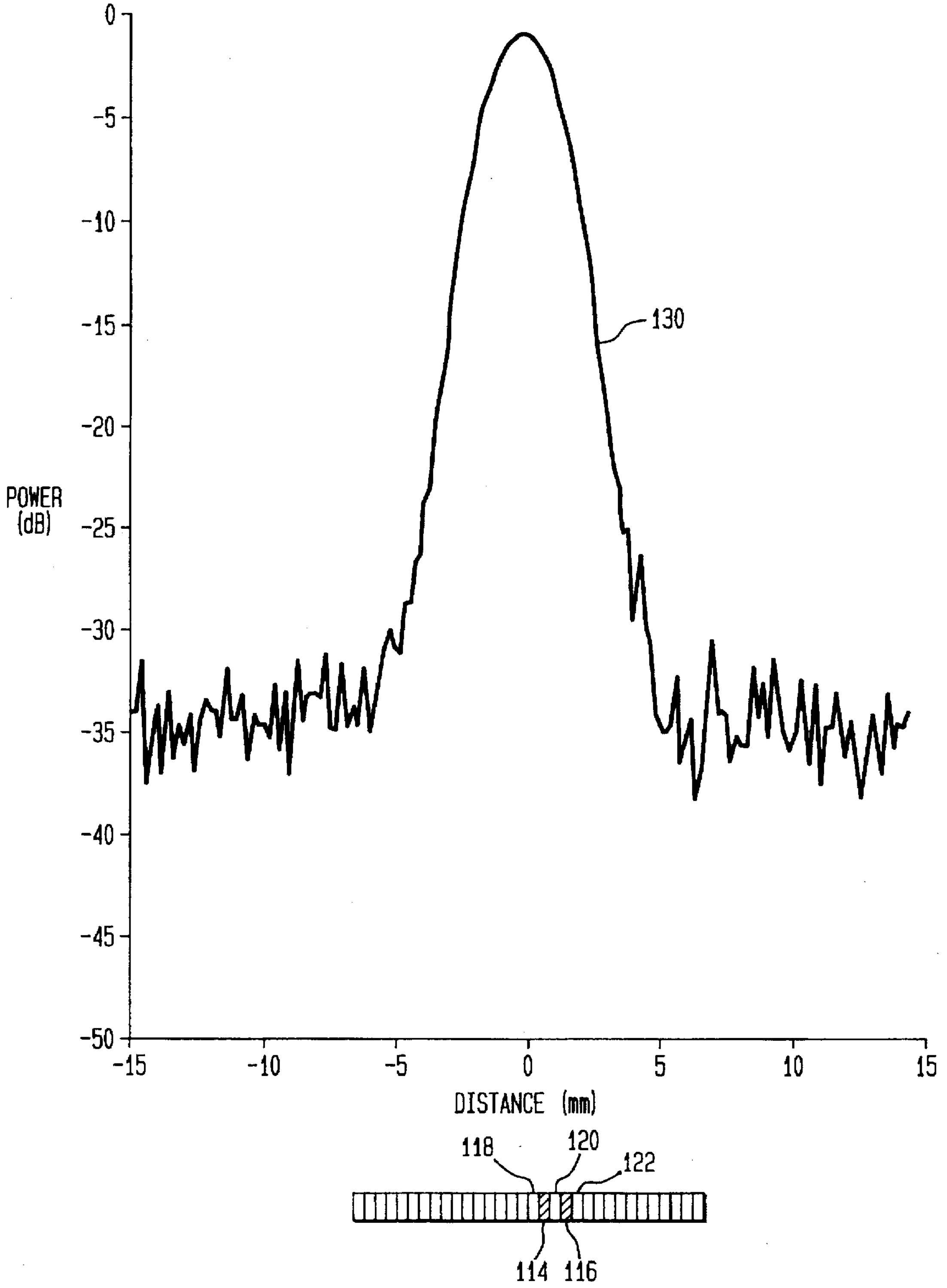
FIG. 5 is a graph illustrating an improved beam pattern created when a transducer with inoperative elements is compensated by the method of the present invention.

FIG. 5 illustrates the improvement in the beam profile obtained using the compensation method according to the present invention. Again, the graph shown in FIG. 5 is a computer simulation assuming a transducer with thirty-two elements, all of which are driven with the same driving signal of FIG. 3A used to create the ultrasonic beam and that two elements, 114 and 116, are inoperative. The inoperative elements 114 and 116 are separated by a single operative element 120. In the simulation, the transmit voltage/receive gain of both elements 114 and 116 was to be 1.0 if they were waiting.

To compensate for the inoperative elements, the transmit voltage of element 118, which is adjacent and to the left of the inoperative element 114, is increased from 1.0 to 1.5. The gain of an element 120, which is disposed between the inoperative elements 114 and 116, is increased from 1.0 to 2.0 (0.5 for element 114 plus 0.5 for element 116). Finally, the transmit voltage/receive gain of element 122, which is adjacent and to the right of inoperative element 116, is increased from 1.0 to 1.5. Using the increased transmit voltages and receive gains, an ultrasonic beam 130 is created having a beam pattern that more closely matches that shown in FIG. 3A. The beam 130 has relatively steep skirts with the beam power at a point outside 5 millimeters from the center of the beam being at least −30 dB below the peak beam power.

As will be appreciated from the above description, the present invention operates to compensate for inoperative elements in an ultrasound transducer by increasing the transmit voltage and receive gain for the transducer elements that are adjacent the inoperative elements. Presently, a linear interpolation is used to divide the transmit voltage/receive gain among the adjacent elements. However, more sophisticated techniques could be used depending upon the focal depth of the beam. For example, it may be advisable to divide the transmit voltage/gain of the inoperative element unequally between the two or more adjacent elements. Such division could be achieved logarithmically, sinusoidally, etc. In addition, the present invention is not limited to transducers having a single array of transducer elements. Some transducer elements may be arranged to have more than two adjacent elements. In this case, the transmit voltage/gain of each operative element is increased to compensate for the inoperative element.

With the beam pattern narrowed by the compensation system of the present invention, the resulting ultrasound image created will be sharper and more defined than the image obtained using the uncompensated beam profile shown in FIG. 3B. This increased resolution allows a physician or sonographer to better identify and characterize body matter in the patient.

The embodiments of the invention in which an exclusive property or privilege is claimed are defined as follow:

1. A method of generating an ultrasonic beam from an ultrasound transducer of the type having a plurality of transducer elements, the method comprising:

determining whether each of the transducer elements in the ultrasound transducer is generating an echo signal in response to a received echo;

locating one or more inoperative transducer elements in the ultrasound transducer;

determining the transmit voltage of a driving signal that would be applied to the inoperative transducer elements if they were working; and supplying a driving signal with an increased transmit voltage to a transducer element that is adjacent the inoperative transducer elements to compensate for the inoperative transducer element.

2. The method of claim 1, wherein the increase in the transmit voltage of the driving signal that is applied to the transducer element that is adjacent the inoperative transducer element is determined by dividing the transmit voltage of the driving signals that would be applied to the inoperative element equally among the adjacent operative transducer elements.

3. The method of claim 1, wherein the echo signals produced by the transducer elements are amplified, the method further comprising:

increasing the amplification of the echo signals produced by the transducer elements that are adjacent the inoperative element.

4. An ultrasound system, comprising:

an ultrasound transducer having a plurality of transducer elements that receive driving signals to produce an ultrasonic signal and produce electronic echo signals in response to a received echo;

a pulse generator selectively coupled to the ultrasound transducer, that produces a series of driving signals that are applied to the plurality of transducer elements to form a beam of ultrasonic energy;

a digital-to-analog converter selectively coupled to the transducer, that receives the electronic echo signals produced by the plurality of transducer elements in response to a received echo; and a processor that is programmed to:

determine whether each of the transducer elements in the ultrasound transducer is generating electronic echo signals in response to a received echo;

locate one or more inoperative transducer elements in the ultrasound transducer;

determine the transmit voltage of a driving signal that would be applied to the one or more inoperative transducer elements if they were working; and supply a driving signal with an increased transmit voltage to those transducer elements that are adjacent the inoperative transducer elements.

5. The ultrasound system of claim 4, wherein the increased transmit voltage of the driving signals applied to the transducer elements that are adjacent the inoperative elements is determined by dividing the transmit voltage of the driving signals that would be applied to the inoperative element equally among an adjacent operative transducer element.

* * * * *